US007553853B2

(12) United States Patent  (10) Patent No.: US 7,553,853 B2
Overeem et al.  (45) Date of Patent: Jun. 30, 2009

(54) SOLID-STATE MONTELUKAST

(75) Inventors: Arjanne Overeem, Ede (NL); Dennie J. M. van den Heuvel, Boxmeer (NL)

(73) Assignee: Synthon BV, Nijmegen (NL)

( * ) Notice: Subject to any disclaimer, the term of this patent is extended or adjusted under 35 U.S.C. 154(b) by 534 days.

(21) Appl. No.: 10/960,639

(22) Filed: Oct. 8, 2004

(65) Prior Publication Data

US 2005/0107426 A1   May 19, 2005

Related U.S. Application Data

(60) Provisional application No. 60/509,957, filed on Oct. 10, 2003.

(51) Int. Cl.
*C07D 215/12* (2006.01)
*A61K 31/47* (2006.01)
(52) U.S. Cl. ..................................... 514/311; 546/174
(58) Field of Classification Search .................. 546/174; 514/311
See application file for complete search history.

(56) References Cited

U.S. PATENT DOCUMENTS

| 5,266,568 | A | | 11/1993 | Belley et al. |
| 5,270,324 | A | | 12/1993 | Zamboni et al. |
| 5,428,033 | A | * | 6/1995 | Belley et al. ............. 514/228.2 |
| 5,523,477 | A | | 6/1996 | King et al. |
| 5,565,473 | A | | 10/1996 | Belley et al. |
| 5,585,115 | A | | 12/1996 | Sherwood et al. |
| 5,614,632 | A | | 3/1997 | Bhupathy et al. |
| 5,856,322 | A | | 1/1999 | Belley et al. |
| 5,869,673 | A | | 2/1999 | Tung et al. |
| 6,063,802 | A | | 5/2000 | Winterborn |
| 6,320,052 | B1 | | 11/2001 | Bhupathy et al. |
| 2004/0265375 | A1 | | 12/2004 | Platteeuw et al. |
| 2005/0107612 | A1 | | 5/2005 | Reguri et al. |
| 2005/0187243 | A1 | | 8/2005 | Niddam-Hildesheim et al. |
| 2005/0234241 | A1 | | 10/2005 | Sundaram et al. |
| 2005/0245568 | A1 | | 11/2005 | Overeem et al. |
| 2005/0245569 | A1 | | 11/2005 | Overeem et al. |
| 2006/0004204 | A1 | | 1/2006 | Reguri et al. |

FOREIGN PATENT DOCUMENTS

| CN | 1420113 | * | 5/2003 |
| CN | 1428335 | * | 7/2003 |
| EP | 0 480 717 | | 4/1992 |
| WO | WO 95/18107 | | 7/1995 |
| WO | WO 03/066598 | * | 8/2003 |
| WO | WO 03/066598 A1 | | 8/2003 |
| WO | WO 2004/108679 A1 | | 12/2004 |
| WO | WO 2005/040123 A1 | | 5/2005 |
| WO | WO2005040123 | * | 5/2005 |

OTHER PUBLICATIONS

"An Efficient Synthesis of LTD₄ Antagonist L-699,392" by A.O. King et al., *J. Org. Chem.* 1993, 58, pp. 3731-3735.

* cited by examiner

*Primary Examiner*—D. Margaret Seaman
(74) *Attorney, Agent, or Firm*—Mark R. Buscher

(57) ABSTRACT

A solid form of a compound of formula 1:

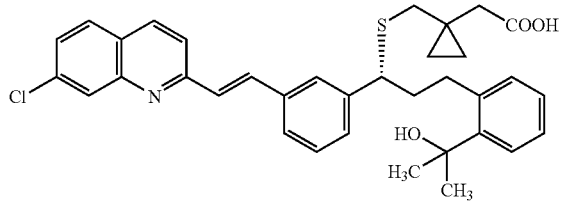

is provided. The compound of formula 1 can be obtained in solid state by precipitation from a solution containing the same. The compound is useful as leukotriene antagonist and can be formulated into a pharmaceutical composition that also includes a pharmaceutically acceptable excipient.

32 Claims, 3 Drawing Sheets

SOLID-STATE MONTELUKAST

This application claims the benefit of priority under 35 U.S.C. § 119(e) from U.S. provisional patent application Ser. No. 60/509,957, filed on Oct. 10, 2003, the entire contents of which are incorporated herein by reference.

BACKGROUND OF THE INVENTION

The present invention relates to solid-state montelukast, pharmaceutical compositions comprising the same, as well as to processes of making and using the same.

Montelukast, chemically [R-(E)]-1-[[[1-[3-[2-(7-chloro-2-quinolinyl)ethenyl]phenyl]-3-[2-(1-hydroxy-1-methyl-ethyl)phenyl]propyl]thio]methyl]cyclopropane acetic acid, has the following structure of formula (1):

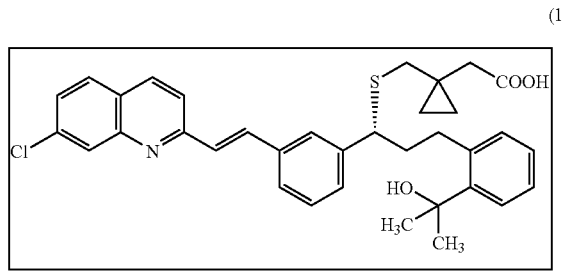

(1)

Montelukast monosodium salt (montelukast sodium) is commonly used for treatment of asthma. It is marketed under the brand name SINGULAIR® (Merck) in the form of oral tablets, chewable tablets, and granules. The structure of montelukast sodium corresponds to formula (2):

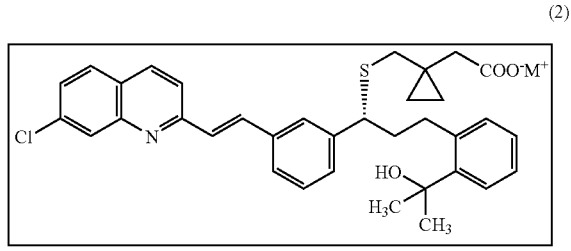

(2)

wherein $M^+$ represents a sodium cation. Montelukast sodium is a hygroscopic, white to off-white powder that is freely soluble in ethanol, methanol, and water and practically insoluble in acetonitrile.

Although several patents relate to montelukast and related compounds, no patent shows the isolation, crystallization or precipitation of solid montelukast, that is the acid, but rather only a salt of montelukast is shown to be obtained in solid state. For example, U.S. Pat. No. 5,565,473 to BELLEY et al. (see also corresponding EP 0 480 717) discloses a genus of pharmaceutically useful compounds that encompasses montelukast and salts thereof. Example 161 of BELLEY et al. purports to make the sodium salt of montelukast via the free acid. However, neither the formation of the free acid, nor the salt, is shown in detail. Instead, the remainder of the synthesis is stated to be carried out under the procedure of steps 10-12 of Example 146. According to Example 146, the (analogous) acid is not rendered or isolated in a solid form but rather the acid remains in an oil form and/or in solution. Only the sodium salt is isolated in solid state. Thus, BELLEY et al. fails to show obtaining a solid state montelukast.

Similarly, WO 95/18107 discloses methods of preparing, inter alia, montelukast and it salts, but does not disclose montelukast, i.e., the free acid, isolated in solid state. Instead, according to the preferred embodiment, and Example 7, the montelukast is converted in situ to the readily isolatable crystalline dicyclohexylamine salt and then subsequently converted to the sodium salt. According to WO 95/18107 this offers a simple and efficient method for the purification of montelukast and for the preparation of the crystalline montelukast sodium.

A similar disclosure is found in U.S. Pat. No. 5,523,477 to KING et al. Example 2 shows the formation of montelukast and conversion into the dicyclohexylamine salt, which is then precipitated. Example 3 shows the conversion of the montelukast dicyclohexylamine salt to sodium montelukast by dissolving the solid dicyclohexylamine salt in toluene and adding acetic acid to reform the free acid. Then to the organic layer containing the acid (montelukast) was added NaOH. Solid state montelukast is not reported to be formed.

While the known montelukast sodium is isolatable in solid state, it suffers from various disadvantages. It is hygroscopic and easily absorbs up to 3 equivalents of water. It is also not stable in aqueous solutions as a precipitate may be formed after certain time. In such solutions it is surface active i.e., its behavior resembles a soap, which can cause problems in granulation processes for making tablets. It would be desirable to have a pharmaceutically active form of montelukast that can be easily obtained in solid form and preferably having some improvement over the known sodium montelukast.

SUMMARY OF THE INVENTION

The present invention includes the surprising discovery that montelukast (i.e., the compound of formula (1)) may be isolated in a solid form; e.g., a crystalline form or an amorphous form. Accordingly, a first aspect of the invention relates to a solid form of a compound of formula 1:

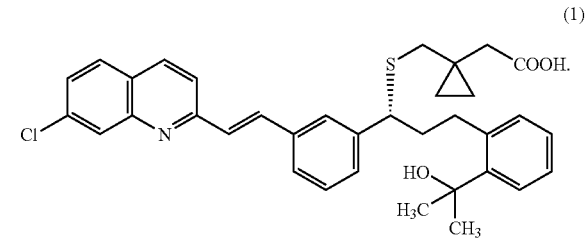

(1)

Another aspect of the invention relates to a pharmaceutical composition, comprising the solid compound according to formula 1 and at least one pharmaceutically acceptable excipient. In particular, such a composition is a solid composition and, in a preferred aspect, the composition is adapted for oral administration.

Yet another aspect of the invention relates to a method that comprises administering an effective leukotriene antagonist amount of the solid compound of formula 1 to a patient in need thereof.

Another aspect of the invention relates to a process that comprises providing a solution of a compound of formula 1:

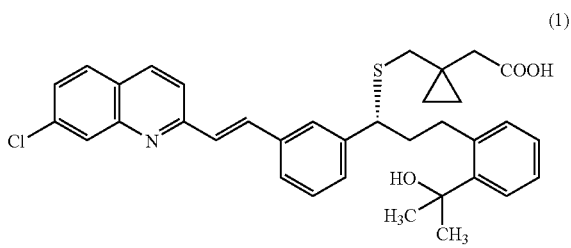

in a solvent, and precipitating the compound of formula 1 from the solution to form a solid precipitate that contains the compound. The solvent may be selected from aromatic hydrocarbons, alcohols, ethers, halogenated hydrocarbons, organic acids, water, and combinations thereof.

A further aspect of the invention relates to a method, which comprises synthesizing montelukast in a solution; precipitating the montelukast to obtain a solid montelukast; dissolving and/or dispersing the montelukast in a solvent; converting the montelukast to a sodium salt of montelukast; and isolating the sodium salt of montelukast in solid form. This method is useful for, inter alia, obtaining purified sodium montelukast.

DESCRIPTION OF THE INVENTION

The present invention relates to the surprising discovery that montelukast can be isolated in a solid state or form. Furthermore, solid montelukast has advantageous properties, most notably reduced hygroscopicity, in comparison to sodium montelukast.

The solid form of montelukast, i.e., the compound represented by formula (1)

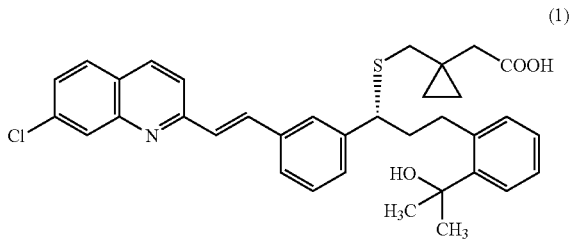

can be any state or form of montelukast that is solid and specifically includes crystalline and amorphous forms. The solid form may also be a mixture of solid forms such as a mixture of crystalline forms, a mixture of amorphous and crystalline forms, etc. Further, solid montelukast can be a solvate including a hydrate, or an anhydrate. Preferably the solid montelukast is anhydrous. For purposes of the present invention, an anhydrate can have a small amount of water but typically 0.5% by weight or less. Typically the solid montelukast is yellow to pale yellow in color, which is in contrast to the off-white color of sodium montelukast.

The solid montelukast is, in some embodiments, substantially pure; that is, substantially free from impurities. In this regard, the solid montelukast is preferably at least about 90 wt %, more preferably at least 95 wt %, still more preferably at least 97 wt %, 98 wt %, or at least 99 wt % pure. As a pharmaceutical active agent, the solid montelukast is preferably of high purity such as at least 99.5 wt %, or at least 99.9 wt % pure compound of formula (1). Correspondingly the level of impurities may be less than about 10 wt %, 5 wt %, 3 wt %, 2 wt %, 1 wt %, 0.5 wt %, or 0.1 wt %.

The solid montelukast is preferably essentially free from montelukast salts, such as montelukast sodium salt. Specifically, the solid montelukast preferably has less than about 10 wt %, more preferably less than 5 wt %, still more preferably less than 1 wt %, and most preferably less than 0.1 wt % of any montelukast salt(s). Similarly, the solid montelukast is preferably substantially free from residual solvents such as solvents used in making the solid montelukast. The residual solvent content may be less than about 10 wt %, preferably less than 2 wt %, and most preferably less than 1 wt %, 0.5 wt %, or 0.1 wt %.

Figure 1:
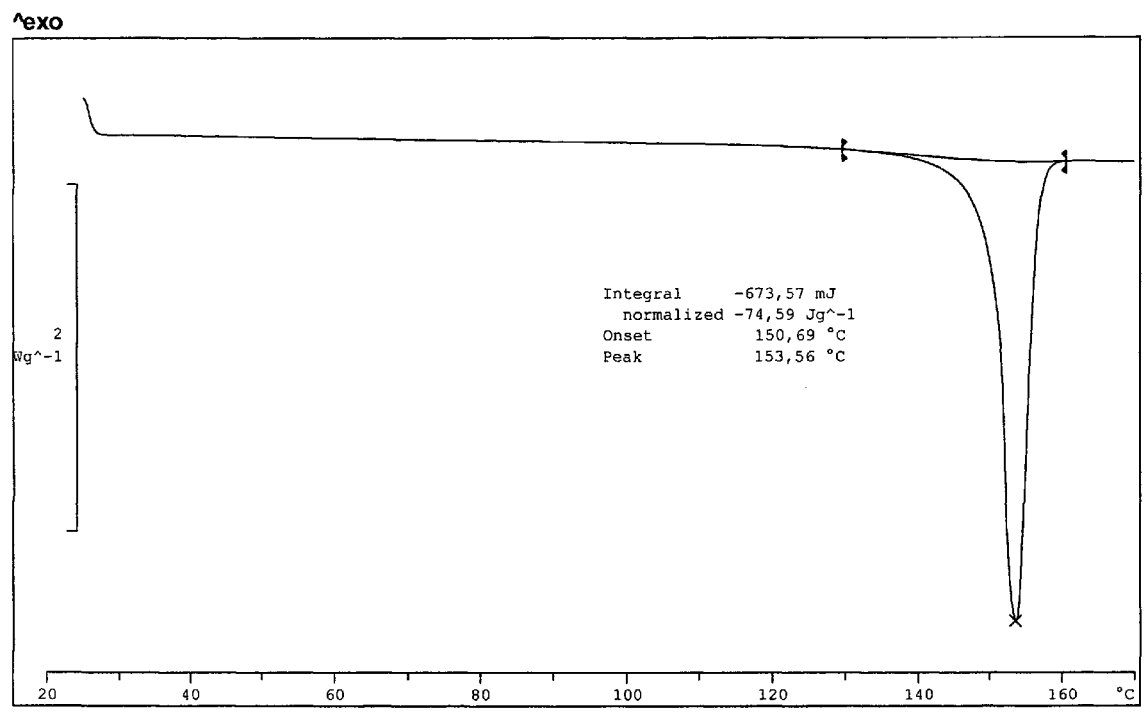
FIG. 1 is a DSC curve of crystalline montelukast produced in Example 1.
Figure 2:
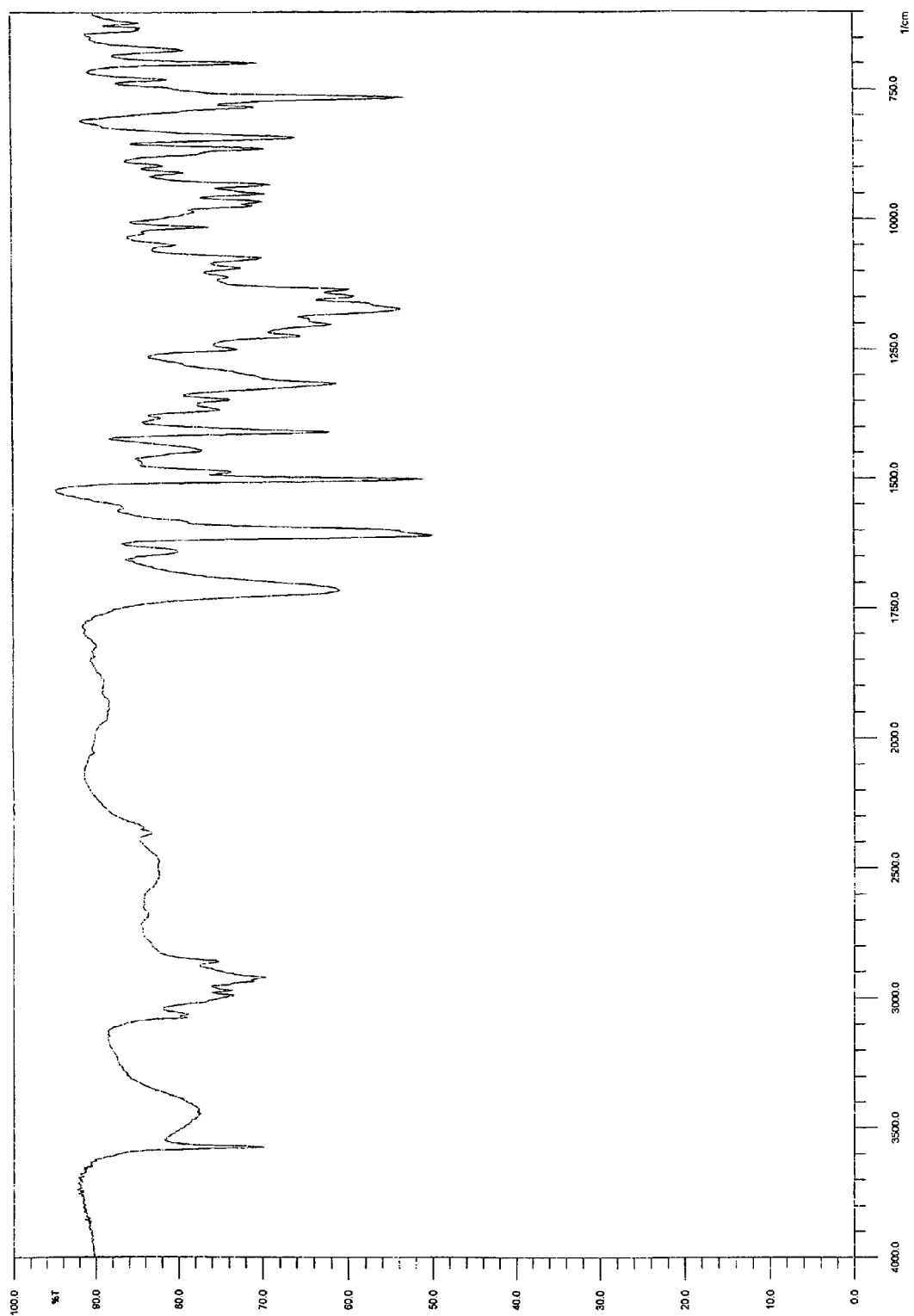
FIG. 2 is an IR spectrum of crystalline montelukast produced in Example 1.
Figure 3:
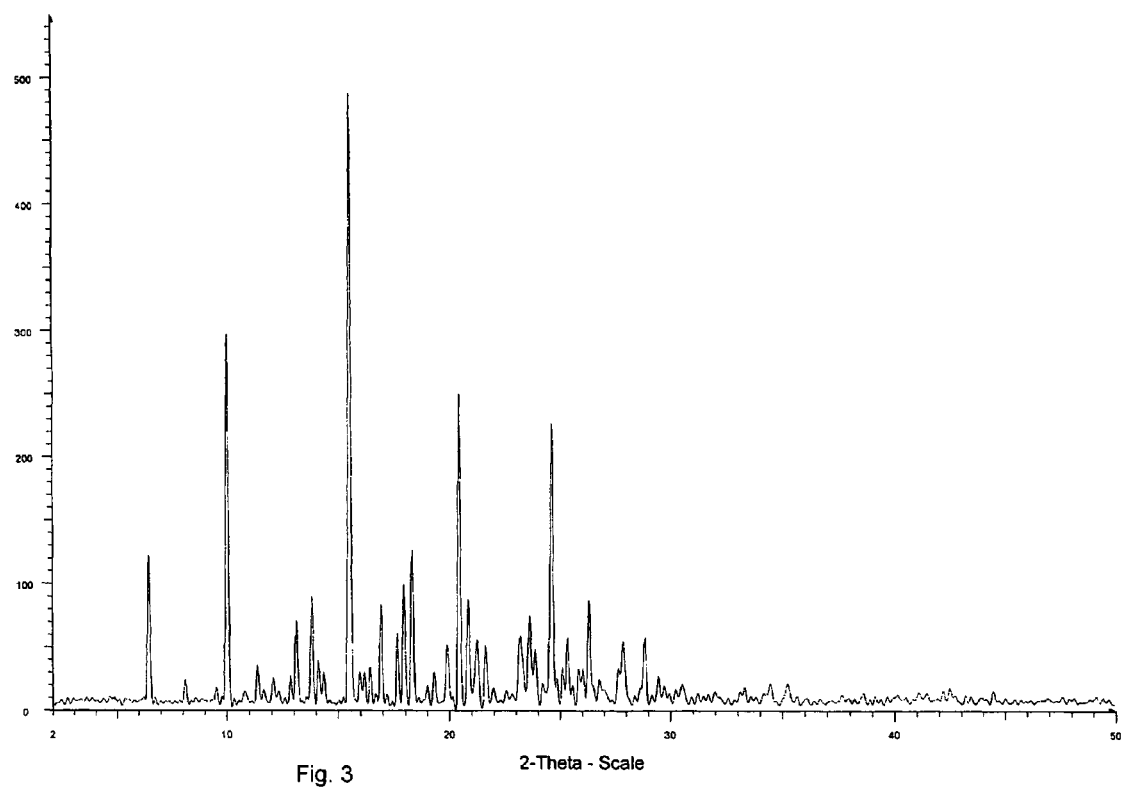
FIG. 3 is an X-Ray Powder Diffraction Pattern of crystalline montelukast produced in Example 1.

The solid montelukast can be crystalline. A preferred crystalline form exhibits melting within the range of 148° C.-158° C.; i.e., at a temperature or temperature range within the range of 148° C. to 158° C. Preferably, the crystalline montelukast exhibits a melting endotherm peak under differential scanning calorimetry (DSC) analysis at 5° C./min at one or more temperatures within the range of 150° C.-158° C., preferably 152° C.-158° C., and in some embodiments about 156° C.-158° C. especially about 156° C. or about 157° C., each +/− 0.5° C. The melting point or range as well as the DSC peak can vary based on differences in crystalline form, i.e. polymorphs, differences in bound solvents, i.e. pseudomorphs, and impurity types and amounts. An example of a preferred crystalline montelukast has a DSC curve as shown in FIG. 1 and/or an IR spectra as shown in FIG. 2 and/or an X-Ray Powder Diffraction Pattern as shown in FIG. 3

The solid montelukast can also be amorphous, including partly amorphous. Generally an amorphous-containing solid form of montelukast exhibits melting within the range from about 60° C. to 160° C., and typically begins melting at a temperature within the range of 60° C. to 100° C. Amorphous montelukast is generally more water-soluble than crystalline montelukast, which can be advantageous, such as in an immediate release oral dosage form. The amorphous montelukast also has good tabletting properties and can provide an advantageous dissolution profile in a solid dosage form.

The present invention also includes the discovery of processes of making solid forms of montelukast. Generally the process comprises providing a solution comprising a compound of formula 1:

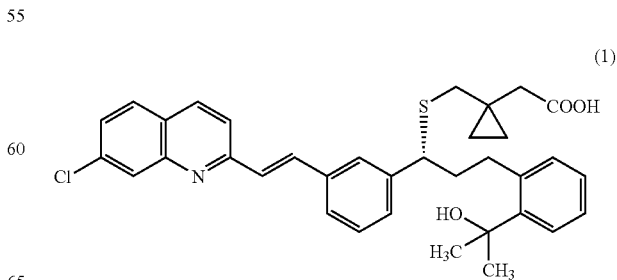

dissolved in a solvent; and precipitating the compound of formula 1 from the solution to form a solid precipitate which contains the compound. The solvent is selected from the group consisting of aromatic hydrocarbons (e.g., toluene, benzene), alcohols (e.g., methanol, ethanol, isopropanol), ethers (e.g., dioxane, tetrahydrofuran), ketones (e.g., acetone), halogenated hydrocarbons (e.g., dichloromethane), organic acids (e.g., acetic acid), water, and combinations thereof. The aromatics typically contain 6 to 20 carbon atoms while the alcohols, ethers, ketones, halogenated hydrocarbons, and organic acids typically have 1 to 12 carbon atoms preferably 1-8 carbon atoms. The solvent can be a single species or a combination of two or more species, i.e. a solvent system. A preferred solvent is toluene.

"Providing" the montelukast-containing solution can be accomplished by any step or combination of steps that result in the montelukast solution, even if only temporarily. For example, the montelukast solution can be provided by simply dissolving montelukast or a product comprising montelukast in the solvent. Alternatively, the montelukast solution can be provided by forming the montelukast in situ by a chemical synthesis in the solvent. Synthesizing includes such reactions as neutralizing a montelukast salt, which is discussed in more detail below, as well as completing an organic synthesis of the montelukast molecule. The montelukast molecule can be prepared by any suitable process including, but not limited to, those organic syntheses described in BELLEY et al and KING et al. Thus any way which results in montelukast dissolved in a solvent is contemplated as meeting the "providing" step.

The dissolved montelukast is precipitated from the solution by any suitable means or techniques in order to produce a montelukast-containing precipitate. The precipitate can be amorphous, partly amorphous, or crystalline. The providing and precipitating steps may occur simultaneously, in an overlapping fashion, or sequentially including with significant time lapse between providing the montelukast solution and precipitating the montelukast, i.e., a storage period between the steps. All such possibilities are contemplated as being within the present invention. Accordingly, the precipitation may occur spontaneously based on the solvent used in the solution, the temperature of the solution, and/or the concentration of the montelukast, etc., or the precipitation may be induced, e.g., by reducing the temperature of the solvent, by reducing the volume of the solution, by adding a seed, etc. It should be noted that in some embodiments, both spontaneous and induced precipitation are carried out in the precipitating step. Additionally, a contrasolvent (a solvent in which the montelukast is less soluble) may be added to assist and/or cause precipitation to begin or to improve the yield and can be added before, during or after precipitation begins. The precipitation step is not particularly limited in terms of time but generally ranges from immediate to several hours, usually not more than six hours.

Generally, the temperature during the precipitation step is not limited and typically ranges from 0° C. to less than the reflux temperature of the solvent. The temperature need not remain constant during the precipitation step. In some embodiments, usually in conjunction with the providing of the montelukast solution, the solution is heated to greater than ambient temperature, e.g., greater than 25° C., preferably greater than 40° C., up to the reflux temperature of the solution and then cooled. During the cooling precipitation begins. Larger precipitate, which is easier to filter, is often obtained by precipitating at an elevated temperature.

After the precipitation, the solid montelukast is normally separated from the solution or solvent by conventional means including filtration, optionally with drying. In this way a dry, solid montelukast material is obtained.

As mentioned above, a neutralization reaction is a convenient way to provide montelukast in solution. The process of neutralization involves reacting a salt of montelukast such as a compound of formula (2) wherein M is a cation with an acid to obtain the montelukast of formula (1). The salt of montelukast can be prepared from bases including inorganic bases and organic bases. Salts derived from inorganic bases include salts of aluminum, ammonium, calcium, copper, ferric, ferrous, lithium, magnesium, manganic, manganous, potassium, sodium, zinc, and the like. Salts derived from organic non-toxic bases include salts of primary, secondary, and tertiary amines, substituted amines including naturally occurring substituted amines, cyclic amines (e.g., dicyclohexylamine), and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Thus M in formula (2) can be the corresponding cation of any of the above bases.

The acid used in this process may be an organic or inorganic acid, and is preferably acetic acid. Completion of the neutralization reaction may be monitored, e.g., by measuring pH. At the completion of neutralization, the pH may range from about 3 to 7, such as 4.5 to 6.0.

The neutralization reaction can be carried out in a monophasic or multiphasic system. A monophasic system comprises a single solvent or a mixture of mutually miscible solvents in which the resulting montelukast is preferably only sparingly soluble and may thus readily precipitate and be separated from the remaining liquid. The solvent system may be selected so that the starting montelukast salt and the neutralization acid are soluble in the solvent system, at least at an elevated temperature, but this is not required.

The solvent system may also be multi-phasic, e.g., biphasic. For instance, the neutralization reaction may proceed in a first, essentially aqueous phase, and the product of the reaction may be extracted into a second phase that is immiscible with the first, while the rest of the reagents and the salt co-product remain in the first phase. After separation of the phases, the montelukast precipitates from the solution in the second phase, basically as described above. Additional phases may be used to improve the purity of the product.

In this regard, the solvent system may dissolve impurities. For example, the solvent system may dissolve the co-product of the reaction, i.e., the salt of the neutralizing acid and the cation of the montelukast salt, so that the montelukast precipitates free from this co-product. Still further, the solvent may dissolve side-products and colored impurities that are generally present in the starting montelukast salt.

In another aspect, the montelukast salt may be dissolved or suspended in one part of the solvent system, and a solution or suspension of the neutralizing acid may be in another part of the solvent system. For instance, the montelukast salt may be added portionwise to the solvent system until the reaction is completed. The composition of both parts of the solvent system may be identical or different.

The process of forming solid montelukast is also useful as a purification technique. The raw montelukast formed in an organic synthesis solution can be precipitated to remove undesired co-products and/or reactants from the montelukast. Alternatively, a montelukast salt, even one that has already been precipitated, may be subjected to the process of the present invention, i.e. via the neutralization process, to further purify the montelukast. It should be noted that the solvent and precipitation conditions used to precipitate the montelukast are frequently different from the solvent and conditions used to precipitate the montelukast salt, thereby allowing for the removal of different impurities and/or different proportions of impurities by the precipitation as montelukast. Any of the above-described precipitation conditions can be used including mono-phasic and multi-phasic systems. Once the solid montelukast is formed, it can be dissolved and/or dispersed in a solvent and converted to a salt, especially a sodium salt, by reacting with a base. In this way, the solid montelukast is used as an intermediate in the purification and/or isolation process of a montelukast salt. Such salts, especially a sodium salt, can be useful in making pharmaceuticals and thus need high purity. A preferred solvent used in purification is toluene.

The methods of the present invention also allow for production of microcrystalline solid montelukast. The particle size of the precipitated product may be controlled, e.g., by the temperature regimen, nature of the solvent, concentration of the solution, etc. Furthermore, microcrystalline product may be formed by performing the precipitation or crystallization in an ultrasonic bath. Alternatively, montelukast of the desired particle size may be obtained by micronization in micronization equipment known in the art, optionally in combination with sieving.

The resulting solid montelukast of the present invention may have an average particle size of less than 200 microns, such as less than 100 microns, or less than 63 microns. For example, all crystals may be less than 63 microns.

While the precipitate is usually crystalline, it can be amorphous or only partly crystalline. If desired, solid amorphous montelukast can be converted to a crystalline form by (re)crystallization or (re)precipitation from a melt or solution thereof. Crystalline montelukast forms are generally stable and do not convert to the amorphous form. However, it is possible to convert some crystalline montelukast into an amorphous form by slurrying the crystalline montelukast in a suitable solvent.

Montelukast may be formulated into various pharmaceutical compositions. The pharmaceutical compositions may comprise an effective leukotriene antagonist amount of the solid-state montelukast of the present invention as the active ingredient and at least one pharmaceutically acceptable excipient. The solid state montelukast can be crystalline or amorphous. For instance, a suitable pharmaceutical composition may comprise microcrystalline montelukast in admixture with pharmaceutically acceptable excipient(s). In some embodiments, an amorphous montelukast can be advantageous due to its greater aqueous solubility than crystalline montelukast.

Pharmaceutically acceptable excipients are known in the art and include carriers, diluents, fillers, binders, lubricants, disintegrants, glidants, colorants, pigments, taste masking agents, sweeteners, flavorants, plasticizers, and any acceptable auxiliary substances such as absorption enhancers, penetration enhancers, surfactants, co-surfactants, and specialized oils. The proper excipient(s) are selected based in part on the dosage form, the intended mode of administration, the intended release rate, and manufacturing reliability. Examples of common types of excipients include various polymers, waxes, calcium phosphates, sugars, etc. Polymers include cellulose and cellulose derivatives such as HPMC, hydroxypropyl cellulose, hydroxyethyl cellulose, microcrystalline cellulose, carboxymethylcellulose, sodium carboxymethylcellulose, calcium carboxymethylcellulose, and ethylcellulose; polyvinylpyrrolidones; polyethylenoxides; polyalkylene glycols such as polyethylene glycol and polypropylene glycol; and polyacrylic acids including their copolymers and crosslinked polymers thereof, e.g., Carbopol® (B.F. Goodrich), Eudragit® (Rohm), polycarbophil, and chitosan polymers. Waxes include white beeswax, microcrystalline wax, carnauba wax, hydrogenated castor oil, glyceryl behenate, glycerylpalmito stearate, and saturated polyglycolyzed glycerate. Calcium phosphates include dibasic calcium phosphate, anhydrous dibasic calcium phosphate, and tribasic calcium phosphate. Sugars include simple sugars, such as lactose, maltose, mannitol, fructose, sorbitol, saccharose, xylitol, isomaltose, and glucose, as well as complex sugars (polysaccharides), such as maltodextrin, amylodextrin, starches, and modified starches.

The solid montelukast may be formulated into compositions for parenteral administration, oral administration, rectal administration (e.g., suppository), transdermal administration (e.g. transdermal patch), and the like. The compositions for oral administration may be solid or liquid, such as in the form of an oral solution, oral capsule, or an oral tablet. Preferably the solid montelukast is formulated into a solid dosage form, especially an oral solid dosage form or an inhalable solid dosage form optionally with a propellant.

Solid compositions for oral administration may exhibit immediate release or modified and/or extended release of the active substance from the composition. The pharmaceutical compositions comprising solid montelukast may be formulated, for instance, into conventional immediate release tablets or as rapidly orally disintegrable tablets. For example, the orally disintegrating dosage form may contain at least 50% silicified microcrystalline cellulose, as disclosed in U.S. application Ser. No. 10/824,619 entitled "Orally Disintegrating Tablets," filed Apr. 15, 2004, which is herein incorporated by reference. The silicified microcrystalline cellulose is preferably the intimate physical mixture of colloidal silicon dioxide with microcrystalline cellulose as described in U.S. Pat. No. 5,585,115. The amount of silicon dioxide is normally within the range of 0.1 to 20 wt % and more typically 1.25 to 5 wt % such as about 2 wt %. Surprisingly, such an excipient can form a tablet matrix that is orally disintegrating; i.e., the tablet disintegrates in the mouth in 80 seconds or less, preferably 2 to 50 seconds. The amount of silicified microcrystalline cellulose is preferably 50% to 90%, more preferably 60% to 80% based on the weight of the tablet. As another example, the solid montelukast may be formulated into rapidly disintegrable tablets similar to those described in U.S. Pat. No. 6,063,802 to WINTERBORN, which is herein incorporated by reference. Further, chewable tablets are also contemplated as oral tablets for administering solid montelukast.

Tablets containing solid montelukast may be produced by any standard tabletting technique, e.g., by wet granulation, dry granulation, melt granulation, or direct compression. In general, the tabletting methods that do not employ a solvent ("dry processes") are preferred.

The dry granulation procedure typically comprises mixing the solid excipients (except lubricants), compacting the mixture in a compactor (e.g., a roller compactor), milling the compacted mass, screening the milled granules, mixing with a lubricant, and compressing the mixture into tablets.

The direct compression procedure generally comprises mixing the solid excipients and compressing the uniform mixture into tablets.

Montelukast may also be formulated by melt granulation, i.e., in an admixture with a functional excipient (e.g., glyceryl behenate) that melts at elevated temperature and forms a granulateable melt that is granulated in suitable equipment.

The relative amount of the montelukast in the tablet mass may range from 1 to 10 wt %, such as 2 to 5 wt %.

Montelukast may also be blended into compositions that are suitable for being formulated into pellets by known pelletization techniques. A plurality of montelukast pellets comprising a single dose of montelukast may be encapsulated into capsules made from pharmaceutically acceptable material, such as hard gelatin. In another mode, a plurality of pellets may be compressed together with suitable binders and disintegrants to a disintegrable tablet that, upon ingestion, decomposes and releases the pellets. In yet another mode, the plurality of pellets may be filled into a sachet.

Immediate release solid oral compositions comprising montelukast have the following release profile: more than 80% of the active is released in 30 minutes, preferably in 15 minutes, when measured by the paddle method of Ph.Eur at 50 rpm in 0.01 M HCl in a normal vessel or, alternately, in a peak vessel according to Van Kel.

Tablets or pellets may be coated by a suitable film coat, which may be a film coat (dissolvable in the stomach) or an "enteric coat" (not dissolvable in the stomach). Alternatively, the tablets or pellets may be uncoated.

Montelukast may also be formulated as a molecular dispersion. In such a case, montelukast may be mixed in a suitable solvent with a suitable pharmaceutically acceptable polymer such as polyvinylpyrrolidone, and the mixture may be evaporated to form a solid dispersion. Such a dispersion may have good solubility in aqueous media and good bioavailability after oral administration.

The montelukast may be in the form of an inhalable dry powder that is respirable, i.e., suitable for pulmonary delivery. The inhalable powder may comprise solid (i.e., non-solution) particles that are capable of being (i) readily dispersed in or by an inhalation device; and/or (ii) inhaled by a subject so that at least a portion of the particles reach the lungs to permit penetration into the alveoli. The inhalable powder may be contained within a capsule or within a canister, optionally with a propellant such as in a traditional inhaler.

The pharmaceutical dosage forms formulated from the compositions of the invention may comprise a unit dose of montelukast, i.e., a therapeutically effective amount of montelukast for a single dose administration. The amount of the montelukast base in the unit dose may range from 0.1 to 100 mg, 1 to 50 mg, or 1 to 20 mg, typically 1-10 mg such as 1, 2, 4, 5, 8, 10, or 20 mg.

The unit dose in tablet form may comprise a single tablet but it may also comprise a divided tablet or several smaller tablets (minitablets) administered at the same time. In the case of minitablets, several smaller tablets may be filled into a gelatin capsule to form a unit dose. The unit dose of pellets in capsule form may comprise a single capsule. The unit dose of the injection solution may be a single vial. Solutions for oral administration may be packed in a multidose package, the unit dose being packaged in a calibrated vessel.

Montelukast is able to antagonize the actions of the leukotrienes. Accordingly, it is useful for preventing or reversing the symptoms induced by the leukotrienes, e.g., in a human subject. This antagonism of the actions of leukotrienes indicates that montelukast is useful to treat, prevent, or ameliorate in mammals and especially in humans: (1) pulmonary disorders including diseases such as asthma, chronic bronchitis, and related obstructive airway diseases; (2) allergies and allergic reactions such as allergic rhinitis, contact dermatitis, allergic conjunctivitis, and the like; (3) inflammation such as arthritis or inflammatory bowel disease; (4) pain; (5) skin disorders such as psoriasis, atopic eczema, and the like; (6) cardiovascular disorders such as angina, myocardial ischemia, hypertension, platelet aggregation and the like; (7) renal insufficiency arising from ischemia induced by immunological or chemical (cyclosporin) etiology; (8) migraine or cluster headache; (9) ocular conditions such as uveitis; (10) hepatitis resulting from chemical, immunological, or infectious stimuli; (11) trauma or shock states such as burn injuries, endotoxemia and the like; (12) allograft rejection; (13) prevention of side effects associated with therapeutic administration of cytokines such as Interleukin II and tumor necrosis factor; (14) chronic lung diseases such as cystic fibrosis, bronchitis and other small and large-airway diseases; and (15) cholecystitis.

Thus, montelukast may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatotoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. Montelukast also exhibits cytoprotective action.

The cytoprotective activity of montelukast may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

In addition to montelukast, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like, as disclosed in U.S. Pat. No. 5,565,473 to BELLEY et al., which is herein incorporated by reference.

The present invention is more particularly described and explained by the following non-limiting examples.

EXAMPLES

Example 1

Conversion of Montelukast Sodium into Crystalline Montelukast Acid

Montelukast sodium (0.5 g) was dissolved in a two-phase system containing 10 ml of water and 10 ml of toluene. To the well-stirred solution, 1.2 ml of 1 M acetic acid was added dropwise at room temperature. After 10 minutes, the stirring was stopped, and the mixture was transferred into a separation funnel. The aqueous layer was removed and the yellow organic phase was washed with 10 ml of water, dried with $Na_2SO_4$, filtered, and evaporated to dryness.

The yield was about 300 mg of a light yellow solid. The product was determined to be montelukast acid by $^1$H-NMR. The melting range of the product was determined to be 148-153° C. The product was also analyzed by IR. DSC indicated onset: 150.7° C.; peak: 153.6° C.; and −74.6 $Jg^{-1}$. The water content was determined to be 0.18 wt % by using a Karl Fisher apparatus. These results indicate that the product was crystalline montelukast acid.

Example 2

Conversion of Montelukast Sodium into Montelukast Acid

Montelukast sodium was converted to montelukast by the following scheme:

Montelukast sodium →[$H_2O$/HAc/toluene/(EtOAc)]→ Montelukast acid

The process involved the materials as shown in Table 1, below.

TABLE 1

| Material | MW | Amount | mMol | Molar Ratio |
|---|---|---|---|---|
| Montelukast sodium | 608.18 | 3.0 g | 4.93 | 1 |
| Water | | 45 ml | | |
| Toluene | | 40 ml | | |
| Acetic acid, 1 M | | 7.4 ml | 7.4 | 1.5 |
| Ethyl acetate | | 20 ml | | |

In particular, 3.0 g of montelukast sodium was dissolved in 45 ml of water. After stirring for 5 minutes, 40 ml of toluene was added. To the well-stirred solution, 7.4 ml of 1 M acetic acid was added dropwise at room temperature. After 15 minutes, stirring was stopped and the mixture was transferred into a separation funnel. The aqueous layer was removed. To the yellow organic phase, 20 ml of ethyl acetate was added in order to dissolve some precipitated acid. The organic phase was washed with 50 ml water, dried with $Na_2SO_4$, filtered, and evaporated to dryness, yielding a very intense yellow "foamy" solid. The material was dried overnight under vacuum at 40° C.

The product had a melting range as follows: 60° C.: melting starts; 70° C.: material (partially) molten; 103° C.: recrystallization starts; 125° C.: melting starts; 153° C.: material completely molten. The product was also analyzed by IR. The product had a DSC as follows: exotherm starts >60° C. (broad peak), followed by endotherm with onset: 142.0° C.; peak: 148.3° C.; −31.3 $Jg^{-1}$. The melting range and DSC data indicate that the product was an amorphous material.

Example 3

Conversion of Amorphous Montelukast to Crystalline Montelukast

A DSC cup was filled with some of the (partially) amorphous material of Example 2 and heated at 120° C. for 1 hour. IR analysis indicated that the product was crystalline montelukast acid (light yellow solid).

Example 4

Conversion of Amorphous Montelukast to Crystalline Montelukast

To a 100 ml flask was added part of the (partially) amorphous material of Example 2. Toluene (35 ml) was added, and the mixture was stirred at room temperature overnight. The solid material was then filtered off and dried overnight under vacuum at 40° C., yielding a light yellow solid. The melting range of the product was determined to be 152-155° C. DSC analysis indicated that the product was crystalline montelukast acid.

Example 5A

Hygroscopicity of Montelukast Acid

Montelukast acid (50 mg) from Example 2 was exposed to air overnight. The water content was then determined to be 0.07 wt % using a Karl Fisher apparatus.

Example 5B

Hygroscopicity of Montelukast Acid

Montelukast acid (50 mg) from Example 2 was stored for 2 days at 40° C., 75% relative humidity. The water content was then determined to be 0.27 wt % using a Karl Fisher apparatus.

Example 6

Conversion of Montelukast Sodium into Montelukast Acid

Montelukast sodium was converted to montelukast by the following scheme:

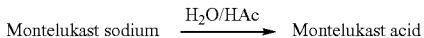

Montelukast sodium →[$H_2O$/HAc]→ Montelukast acid

The process involved the materials as shown in Table 2, below.

TABLE 2

| Material | MW | Amount | mMol | Molar Ratio |
|---|---|---|---|---|
| Montelukast sodium | 608.18 | 5.0 g | 8.22 | 1 |
| Water | | 100 ml | | |
| Acetic acid, 1 M | | 12.33 ml | 12.33 | 1.5 |

In particular, 5 g of montelukast sodium was dissolved in 100 ml of water. To this solution, 12.33 ml of 1 M acetic acid was added dropwise at room temperature. The suspension was stirred for 20 minutes. The acid was filtered off and washed with water. The resulting light yellow solid was dried overnight under vacuum at 40° C.

The yield was 4.6 g. The melting range of the material was rather broad with melting starting slightly at about 90° C.

Example 7

Transformation of Montelukast Acid

The solid product of Example 6 was stirred for 3 hours in toluene, filtered, and dried overnight at 40° C. under vacuum. The resulting crystalline product had a melting range of 150.5-154.8° C.

Example 8

Precipitation of Montelukast Acid from a Low Concentration Solution of Montelukast Sodium in Water Montelukast sodium (200 mg) was dissolved in 60 ml of water and stirred overnight at room temperature, resulting in a white soapy solution with some precipitated material. The mixture was subjected to a first filtration, and a small amount of yellow solid material was isolated and dried overnight under vacuum at 40° C. DSC analysis of the yellow solid indicated that it was not crystalline montelukast acid.

The filtrate from the first filtration was kept overnight at room temperature. It was then subjected to a second filtration, and a very small amount of yellow solid material was isolated and dried overnight under vacuum at 40° C. DSC analysis of this yellow solid indicated that it was not crystalline montelukast acid.

Example 9

Conversion of Montelukast Sodium into Montelukast Acid

Montelukast sodium (3 g) was dissolved in 50 ml of water. To this solution, 7.4 ml of 1 M acetic acid was added dropwise at room temperature. The resulting yellow suspension was stirred for 20 minutes. The acid was filtered off and washed with water. The resulting yellow solid was dried overnight under vacuum at 40° C.

The yield was 2.8 g. The product was determined to be montelukast acid by $^1$H-NMR. The product had a broad melting range with melting starting already at 66° C. and was complete at 225° C. TGA of the product indicated no weight loss. The product was also analyzed by IR and DSC. The product was determined to be amorphous montelukast acid.

Example 10

Treatment of Montelukast Sodium with Hydrochloric Acid in Isopropanol

Montelukast sodium (200 mg) was dissolved in 40 ml of i-propanol. To this solution, 0.24 ml of 5-6 N hydrochloric acid in i-propanol was added dropwise at room temperature. The color of the clear solution changed from colorless to very intense yellow, and the reaction was exothermic. After 10 minutes, a precipitate formed. After 45 minutes of stirring, the suspension was filtered, and the residue was washed with i-propanol. The resulting intense yellow solid was dried overnight under vacuum at 40° C.

The yellow solid was analyzed by IR, DSC, and TGA. The solid could not be analyzed by NMR because part of the material was insoluble in $CDCl_3$. While not wishing to be bound by theory, the yellow solid may be a mixture of montelukast acid and HCl salt (with nitrogen in the quinoline-part of molecule).

Examples 11-20

Recrystallization of Montelukast Acid from Different Solvents

Ten 20 ml flasks were filled with 100 mg (0.17 mmol) of montelukast acid from Example 9. The acid was dissolved in the solvents and with the results shown in Table 3 below.

The flasks were then stored in a cold room held at 4° C. After 4 days of storage in the cold room, the contents of the flasks were as shown in Table 3 below.

TABLE 3

| Example | Solvent | Amount of Solvent (ml) | Immediate Result | Result After 4 Days of Cold Storage |
|---|---|---|---|---|
| 11 | Toluene | 4 | Clear yellow solution | Solid formed |
| 12 | Ethyl acetate | 4 | Clear yellow solution | Small amount of solid formed |
| 13 | Methanol | 4 | Clear yellow solution | Solid formed |
| 14 | Ethanol | 4 | Clear yellow solution | Solid formed |
| 15 | i-Propanol | 4 | Clear yellow solution | Solid formed |
| 16 | Dichloromethane | 4 | Clear yellow solution | Small amount of solid formed |
| 17 | Acetone | 4 | Clear yellow solution | Very fine particles formed |
| 18 | Diethylether | 8 | Hazy solution | Solid formed |
| 19 | Acetonitrile | 10 | Sticky solid (no dissolution of acid) | No change |
| 20 | Acetic acid, glacial | 4 | Clear yellow solution | No change |

After cold room storage, the products of Examples 11, 13, 14, 15, and 18 were filtered and washed, and the solid was dried overnight under vacuum at 40° C. The yields ranged from 75-85 mg.

After the products of Examples 12, 16, 17, 19, and 20 spent 2 more weeks in the cold the status of these Examples was as shown in Table 4 below:

TABLE 4

| Example | Status |
|---|---|
| 12 | Solid was formed; solid was filtered, washed, and dried overnight under vacuum at 40° C. |
| 16 | Solvent was almost completely evaporated; formed solid was filtered, washed, and dried overnight at 40° C. under vacuum |
| 17 | Still (almost) clear solution |
| 19 | Solid was filtered, washed, and dried overnight at 40° C. under vacuum |
| 20 | Still clear solution |

The IR spectra of Examples 11-16, 18, and 19 were substantially identical.

Examples 11-16, 18, and 19 were analyzed by DSC, with the results being summarized in Table 5, below. The DSC of Example 15 included a small peak before its main peak. The melting ranges and water content, as determined by a Karl Fisher apparatus, are also shown in Table 5.

TABLE 5

DSC Results

| Example | Onset (° C.) | Peak (° C.) | Specific Heat of Melting (J/g) | Melting Range (Observed) (° C.) | Water Content (wt %) |
|---|---|---|---|---|---|
| 11 | 151.0 | 152.3 | −81.3 | 151.5-152.8 | 0.17 |
| 12 | 154.7 | 157.5 | −91.5 | 153.2-155.2 | 0.51 |
| 13 | 154.6 | 156.3 | −84.1 | 154.0-155.4 | 0.11 |
| 14 | 155.8 | 157.2 | −79.5 | 154.3-155.2 | 0.09 |
| 15 | 153.1 | 154.7 | −83.6 | 153.8-154.7 | 0.14 |
| 16 | 154.5 | 156.0 | −84.3 | 154.2-155.1 | N/A |
| 18 | 153.8 | 156.1 | −82.6 | 153.1-154.7 | 0.16 |
| 19 | 153.6 | 156.1 | −84.2 | 152.9-154.7 | 0.19 |

Example 21

Montelukast Free Acid Tablets, Orally Disintegrating Tablets

|  | mg/tablet | % |
|---|---|---|
| Montelukast free acid | 9.68 | 9.68 |
| Silicified microcrystalline cellulose | 81.31 | 81.31 |
| L-HPC | 4.94 | 4.94 |
| Aspartame | 2.59 | 2.59 |
| Mint flavour | 0.99 | 0.99 |
| Magnesium stearate | 0.49 | 0.49 |
| Total | 100 | 100 |

Example 22

Montelukast Free Acid Tablets, Orally Disintegrating Tablets

|  | mg/tablet | % |
|---|---|---|
| Montelukast free acid | 10.0 | 9.68 |
| Silicified microcrystalline cellulose | 84.5 | 81.31 |
| L-HPC | 5.0 | 4.94 |
| Sodium stearyl fumarate | 0.5 | 0.49 |
| Total | 100 | 100 |

Example 23

Montelukast Free Acid Tablets, Immediate Release Tablets

|  | mg/tablet | % |
|---|---|---|
| Montelukast free acid | 10.36 | 5.29 |
| Lactose monohydrate | 89.68 | 45.76 |
| Microcrystalline cellulose | 88.99 | 45.40 |
| Crosscarmellose sodium | 5.98 | 3.05 |
| Magnesium stearate | 0.99 | 0.50 |
| Total | 196 | 100 |

In Examples 21-23 above, all excipients, except the lubricant (magnesium stearate or sodium stearyl fumarate), were mixed in a turbula mixer for 15 minutes at 25 rpm. The lubricant was added and the blending was continued for 5 minutes. Tablets were prepared on the Korsch EK-0 tablet press.

Example 24

Montelukast Free Acid Capsules

Capsules are made by filling the composition as described in example 23 into size 3 capsules.

Each of the patents and published patent applications mentioned above are incorporated herein in their entirety. In view of the above description of the invention, it will be readily apparent to the worker skilled in the art that the same may be varied in many ways without departing from the spirit of the invention and all such modifications are included within the scope of the present invention as set forth in the following claims.

What is claimed is:

1. A solid form of a compound of formula 1:

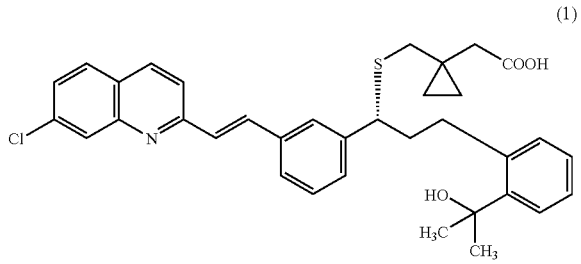

(1)

wherein said solid form is a crystalline form.

2. The solid compound according to claim 1, wherein said crystalline form exhibits melting within the range of 148° C.-158° C.

3. The solid compound according to claim 1, wherein said compound comprises less than 10 wt % of impurities.

4. The solid compound according to claim 1, wherein said compound comprises less than 10 wt % of solvent.

5. The solid compound according to claim 1, which was made by precipitating said compound of formula 1 in crystalline form from a solution containing said compound in dissolved form.

6. A pharmaceutical composition, comprising said solid compound according to claim 1 and at least one pharmaceutically acceptable excipient, wherein said compound is in crystalline form in said composition.

7. The pharmaceutical composition according to claim 6, wherein said composition is a solid oral dosage form containing 1 to 50 mg of said compound of formula 1.

8. The pharmaceutical composition according to claim 7, wherein said solid oral dosage form is an orally disintegrating tablet.

9. A method, of treating asthma or allergic rhinitis, which comprises administering an effective leukotriene antagonist amount of the solid compound of claim 1 to a patient in need thereof.

10. A process, for making a solid precipitate, which comprises providing a solution of a compound of formula 1:

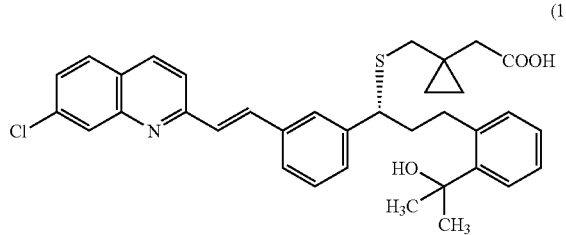

in a solvent; and
precipitating said compound of formula 1 from said solution to form a solid, crystalline precipitate which contains said compound, wherein said solvent is selected from the group consisting of aromatic hydrocarbons, alcohols, ethers, ketones, halogenated hydrocarbons, organic acids, water, and combinations thereof.

11. The process according to claim 10, wherein said providing step comprises dissolving said compound of formula 1 into said solvent.

12. The process according to claim 10, wherein said providing step comprises synthesizing said compound of formula 1 in said solvent.

13. The process according to claim 12, wherein said synthesizing of said compound of formula 1 comprises neutralizing a salt of said compound in said solvent.

14. The process according to claim 12, wherein said synthesizing of said compound of formula 1 comprises completing an organic synthesis of said compound.

15. The process according to claim 10, wherein said precipitating step comprises adding a contrasolvent to said solution.

16. The process according to claim 10, wherein said solvent is selected from the group consisting of toluene, benzene, methanol, ethanol, isopropanol, dioxane, tetrahydrofuran, acetone, dichloromethane, acetic acid, water, and combinations thereof.

17. The process according to claim 10, which further comprises separating said solid crystalline precipitate from said solution.

18. A method, for making sodium montelukast, which comprises:
synthesizing montelukast in a solution;
precipitating said montelukast to obtain a solid crystalline montelukast;
dissolving and/or dispersing said crystalline montelukast in a solvent;
converting said montelukast to a sodium salt of montelukast; and
isolating said sodium salt of montelukast in solid form.

19. The solid compound according to claim 1, wherein said crystalline form is anhydrous.

20. The solid compound according to claim 1, wherein said crystalline form is yellow to pale yellow.

21. The solid compound according to claim 3, wherein said compound comprise less than 1 wt % of impurities.

22. The solid compound according to claim 1, wherein said compound is substantially free of montelukast salts.

23. The solid compound according to claim 1, wherein said crystalline form exhibits a melting endotherm peak under differential scanning calorimetry analysis at 5° C./min at one or more temperatures within the range of 150° C.-158° C.+/− 0.5° C.

24. The solid compound according to claim 1, wherein said crystalline form has an XRPD pattern as shown in FIG. 3.

25. The solid compound according to claim 24, wherein said crystalline form has an IR spectra substantially as shown in FIG. 2.

26. The pharmaceutical composition according to claim 6, wherein said composition is an inhalable solid dosage form.

27. The method according to claim 9, wherein said administering comprises said patient inhaling said effective amount of said solid crystalline compound.

28. The process according to claim 16, wherein said solvent comprises toluene.

29. The method according to claim 18, wherein said solvent is toluene.

30. An inhalable solid dosage form comprising crystalline montelukast and a pharmaceutically acceptable excipient, and optionally further comprising a propellant.

31. The inhalable solid dosage form according to claim 30, wherein the amount of said crystalline montelukast in the dosage form is in a range from 0.1-100 mg.

32. The inhalable solid dosage form of claim 31, wherein the amount of said crystalline montelukast in the dosage form is in a range from 1-10 mg.

* * * * *